(12) United States Patent
Grostefon et al.

(10) Patent No.: US 9,713,531 B2
(45) Date of Patent: Jul. 25, 2017

(54) DEFLECTION RESISTANT ACETABULAR CUP

(71) Applicant: DEPUY SYNTHES PRODUCTS, INC., Raynham, MA (US)

(72) Inventors: Justin D. Grostefon, Columbia City, IN (US); David M. Casey, Mentor, OH (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 0 days.

(21) Appl. No.: 14/872,220

(22) Filed: Oct. 1, 2015

(65) Prior Publication Data

US 2016/0022424 A1    Jan. 28, 2016

Related U.S. Application Data

(62) Division of application No. 13/245,905, filed on Sep. 27, 2011, now Pat. No. 9,180,013.

(51) Int. Cl.
*A61F 2/32* (2006.01)
*A61F 2/30* (2006.01)
*A61F 2/34* (2006.01)

(52) U.S. Cl.
CPC ............ *A61F 2/3094* (2013.01); *A61F 2/34* (2013.01); *A61F 2002/30018* (2013.01); *A61F 2002/30324* (2013.01); *A61F 2002/30329* (2013.01); *A61F 2002/30332* (2013.01); *A61F 2002/30383* (2013.01); *A61F 2002/30563* (2013.01); *A61F 2002/30571* (2013.01); *A61F 2002/30594* (2013.01); *A61F 2002/30604* (2013.01); *A61F 2002/30616* (2013.01); *A61F 2002/30968* (2013.01); *A61F 2002/347* (2013.01); *A61F 2002/3411* (2013.01); *A61F 2002/3429* (2013.01); *A61F 2002/3438* (2013.01); *A61F 2002/3469* (2013.01); *Y10T 29/49826* (2015.01)

(58) Field of Classification Search
CPC ............... A61F 2/34; A61F 2002/3438; A61F 2002/347; A61F 2002/3094
See application file for complete search history.

(56) References Cited

U.S. PATENT DOCUMENTS 5,108,448 A * 4/1992 Gautier .................... A61F 2/34
623/22.26
5,133,758 A   7/1992 Hollister
(Continued)

FOREIGN PATENT DOCUMENTS

EP    1086666 A1    3/2001
EP    1302181 A2    4/2003
(Continued)

OTHER PUBLICATIONS

M. Squire, et al. Acetabular Component Deformation With Press-Fit Fixation; The Journal of Arthroplasty; vol. 21 No. 6 Suppl. 2; 2006, 6 Pages.

*Primary Examiner* — Brian Dukert

(57) ABSTRACT

An acetabular shell for use in hip arthroplasty. The shell includes a first wall having an outer surface, an inner surface, and a rim. The shell further includes a second wall extending from the outer surface of the first wall. The second wall has an outer surface, an inner surface, and a rim. The rim of the second wall is spaced outwardly from the rim of the first wall.

9 Claims, 6 Drawing Sheets

(56) References Cited

U.S. PATENT DOCUMENTS

| | | | |
|---|---|---|---|
| 5,458,650 | A | 10/1995 | Carret |
| 5,549,697 | A | 8/1996 | Caldarise |
| 5,549,700 | A | 8/1996 | Graham |
| 5,641,323 | A | 6/1997 | Caldarise |
| 5,662,158 | A | 9/1997 | Caldarise |
| 5,725,590 | A | 3/1998 | Maumy |
| 5,788,916 | A | 8/1998 | Caldarise |
| 6,610,097 | B2 | 8/2003 | Serbousek |
| 6,811,569 | B1 | 11/2004 | Afriat |
| 6,942,701 | B2 * | 9/2005 | Taylor .................. A61F 2/34 623/22.14 |
| 7,682,399 | B2 | 3/2010 | Shields |
| 7,955,395 | B2 | 6/2011 | Shea |
| 2003/0083751 | A1 | 5/2003 | Tornier |
| 2004/0143336 | A1 | 7/2004 | Burkinshaw |
| 2005/0240276 | A1 | 10/2005 | Shea |
| 2007/0005144 | A1 | 1/2007 | Leisinger |
| 2010/0161072 | A1 * | 6/2010 | Drescher ................ A61F 2/34 623/22.29 |
| 2011/0015753 | A1 | 1/2011 | Meridew |

FOREIGN PATENT DOCUMENTS

| | | |
|---|---|---|
| EP | 1685810 A1 | 8/2006 |
| JP | 2000501009 A | 2/2000 |
| JP | 2007536948 A | 12/2007 |
| JP | 2011147702 A | 8/2011 |

* cited by examiner

DEFLECTION RESISTANT ACETABULAR CUP

CROSS REFERENCE TO RELATED APPLICATION

The present application is a divisional of U.S. patent application Ser. No. 13/245,905 filed Sep. 27, 2011, which is herein incorporated by reference in its entirety.

TECHNICAL FIELD

The present invention relates generally to an implant for use during orthopaedic surgery.

BACKGROUND OF THE INVENTION

A joint within the human body forms a juncture between two or more bones or other skeletal parts. The ankle, hip, knee, shoulder, elbow and wrist are just a few examples of the multitude of joints found within the body. As should be apparent from the above list of examples of joints, many of the joints permit relative motion between the bones. For example, the motion of sliding, gliding, hinge or ball and socket movements may be had by a joint. For example, the ankle permits a hinge movement, the knee allows for a combination of gliding and hinge movements and the shoulder and hip permit movement through a ball and socket arrangement.

The joints in the body are stressed or can be damaged in a variety of ways. For example, the gradual wear and tear is imposed on the joints through the continuous use of a joint over the years. The joints that permit motion have cartilage positioned between the bones providing lubrication to the motion and also absorbing some of the forces directed to the joint. Over time, the normal use of a joint may wear down the cartilage and bring the moving bones in direct contact with each other. In contrast, in normal use, a trauma to a joint, such as the delivery of a large force, from an accident, for example, an automobile accident, may cause considerable damage to the bones, the cartilage or to other connective tissue such as tendons or ligaments.

Arthropathy, a term referring to a disease of the joint, is another way in which a joint may become damaged. Perhaps the best known joint disease is arthritis, which is generally referred to as a disease or inflammation of a joint that results in pain, swelling, stiffness, instability, and often deformity.

There are many different forms of arthritis, with osteoarthritis being the most common and resulting from the wear and tear of cartilage within a joint. Another type of arthritis is osteonecrosis, which is caused by the death of a part of the bone due to loss of blood supply. Other types of arthritis are caused by trauma to the joint while others, such as rheumatoid arthritis, Lupus, and psoriatic arthritis destroy cartilage and are associated with the inflammation of the joint lining.

The hip joint is one of the joints that is commonly afflicted with arthropathy. The hip joint is a ball and socket joint that joins the femur or thighbone with the pelvis. The pelvis has a semispherical socket called the acetabulum for receiving a ball socket head in the femur. Both the head of the femur and the acetabulum are coated with cartilage for allowing the femur to move easily within the pelvis. Other joints commonly afflicted with arthropathy include the spine, knee, shoulder, carpals, metacarpals, and phalanges of the hand. Arthroplasty as opposed to arthropathy commonly refers to the making of an artificial joint. In severe cases of arthritis or other forms of arthropathy, such as when pain is overwhelming or when a joint has a limited range of mobility, a partial or total replacement of the joint within an artificial joint may be justified. The procedure for replacing the joint varies, of course, with the particular joint in question, but in general involves replacing a terminal portion of an afflicted bone with a prosthetic implant and inserting a member to serve as a substitute for the cartilage.

The prosthetic implant is formed of a rigid material that becomes bonded with the bone and provides strength and rigidity to the joint. Cartilage substitute members are chosen to provide lubrication to the joint and to absorb some of the compressive forces. Suitable material for the implant include metals and composite materials such as titanium, cobalt chromium, stainless steel, ceramic and suitable materials for cartilage substitutes include polyethylene. A cement may also be used to secure the prosthetic implant to the host bone.

A total hip replacement, for example, involves removing the ball shaped head of the femur and inserting a stem implant into the center of the bone, which is referred to as the medullary canal, or marrow of the bone. The stem implant may be cemented into the medullary canal or may have a porous coated surface for allowing the bone to heal directly to the implant. The stem implant has a neck and a ball shaped head, which are intended to perform the same functions as a healthy femur's neck and a ball shaped head.

A cup or shell may be positioned directly into the acetabulum. The cup or shell may include a porous coating for promoting bony in-growth to secure the shell to the acetabulum. Alternatively or in addition, the shell may include an opening or a plurality of openings for receiving bone screws to assist in the attachment of the shell to the acetabulum. The cup may be made of a metal, for example, cobalt chromium, stainless steel, or titanium. Alternatively, the cup may be made of a ceramic or of a polyethylene. In some embodiments, the cup directly engages the head. In other embodiments, a liner of some sort is inserted into the cup to articulate against the head. The liner may be made of metal, ceramic, or polyethylene.

When inserting a cup or a shell, the acetabular cavity is often reamed to a size smaller than the shell to be inserted. The shell is then press-fit into the bone. However, such press-fitting can exert loads large enough to deflect the shell. The deflection of the shell can lead to many intra-operative issues that can lead to surgery delay, patient harm, or product dissatisfaction.

Therefore, there is a need for a shell that can be press-fit into an under-reamed acetabular cavity but yet not deflect in such a way to affect the inside of the shell.

SUMMARY OF THE INVENTION

According to one embodiment of the present invention, an acetabular shell for use in hip arthroplasty is provided. The shell includes a first wall having an outer surface, an inner surface, and a rim. The shell further includes a second wall extending from the outer surface of the first wall. The second wall has an outer surface, an inner surface, and a rim. The rim of the second wall is spaced outwardly from the rim of the first wall.

According to another embodiment of the present invention, an acetabular assembly for use in hip arthroplasty is provided. The assembly includes a shell that has a first wall having an outer surface and an inner surface. The outer surface includes a first radius. The shell further includes a second wall extending from the outer surface of the first wall. The second wall has an outer surface and an inner surface. The inner surface has a second radius. The second radius of the inner surface of the second wall is greater than the first radius of the outer surface of the first wall. The assembly further includes a liner adapted to couple to the inner surface of the first wall.

According to yet another embodiment of the present invention, a method of manufacturing an acetabular shell is provided. The method includes manufacturing a first wall of the acetabular shell and manufacturing a second wall of the acetabular shell. The second wall of the acetabular shell is slid over the first wall and the second wall is affixed to the first wall.

BRIEF DESCRIPTION OF THE DRAWINGS

For a more complete understanding of the present invention and the advantages thereof, reference is now made to the following description taken in connection with the accompanying drawings, in which.

DETAILED DESCRIPTION OF THE DRAWINGS

Embodiments of the present invention and the advantages thereof are best understood by referring to the following descriptions and drawings, wherein like numerals are used for like and corresponding parts of the drawings.

Figure 1:
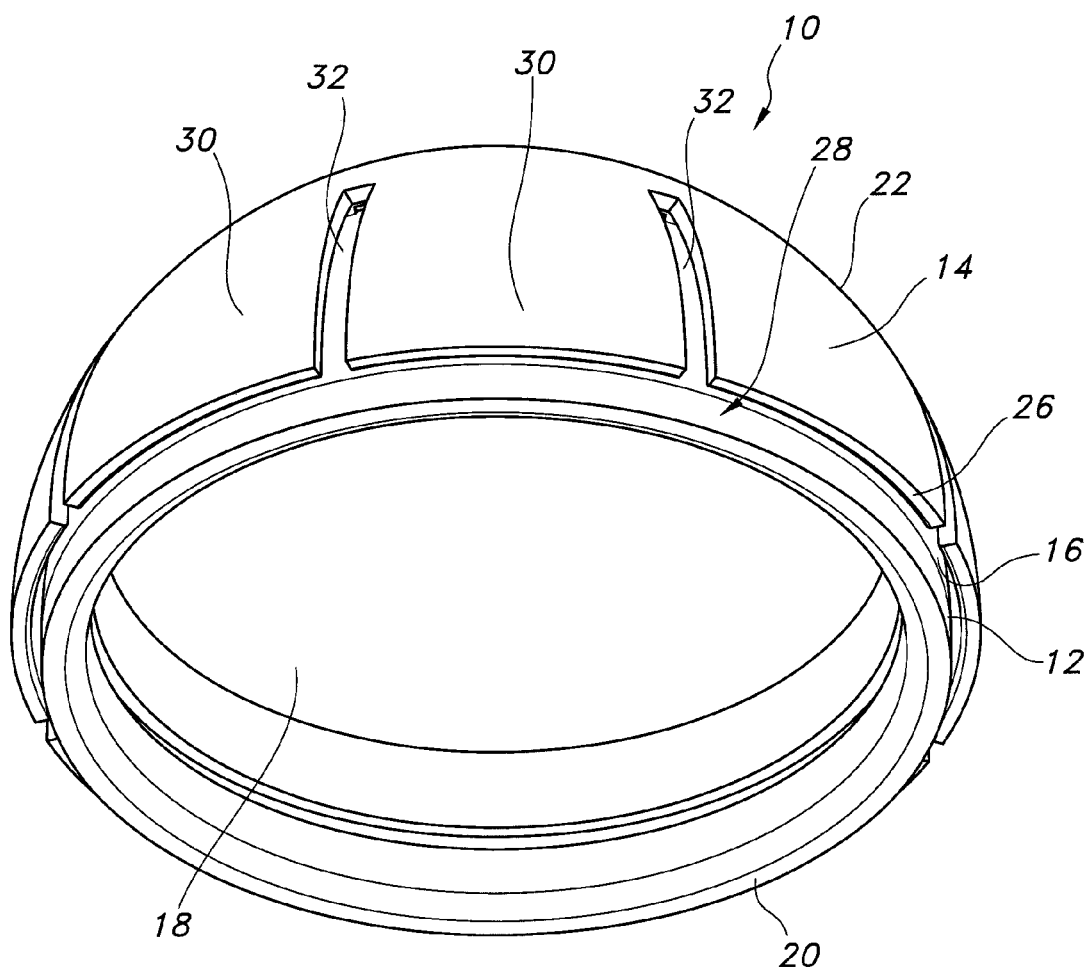
FIG. 1 is a perspective view of the acetabular shell according to one embodiment of the present invention.

Turning now to a FIG. 1, an acetabular shell (or cup) 10 is shown. The acetabular shell 10 includes a first wall 12 and a second wall 14 extending from the first wall 12. The second wall 14 is permanently fixed to the first wall 12. The first wall 12 has an outer surface 16, an inner surface 18, and a rim 20 coupling the two surfaces 16, 18. The second wall 14 includes an outer surface 22, an inner surface 24 (FIG. 2), and a rim 26 coupling the two surface 22, 24. The rim 26 of the second wall 14 is spaced outwardly from the rim 20 of the first wall 12. In other words, there is a recess 28 between the inner surface 24 of the second wall 14 and the outer surface 16 of the first wall 12. The recess 28 allows the second wall 14 to be deflected as it is inserted into a prepared acetabulum without deflecting the first wall 12. This will be more fully explained in detail below.

As shown in FIG. 1, the second wall 14 may include a plurality of outwardly extending flanges 30. The flanges 30 are separated by longitudinal recesses 32. The flanges 30 and recesses 32 allow the second wall 14 to flex when inserted into a prepared acetabulum. In other embodiments, the second wall 14 may not include flanges 30 separated by recesses 32. In those embodiments, the second wall 14 may be a singular generally spherical wall that flexes when inserted into a prepared acetabulum.

Figure 2:
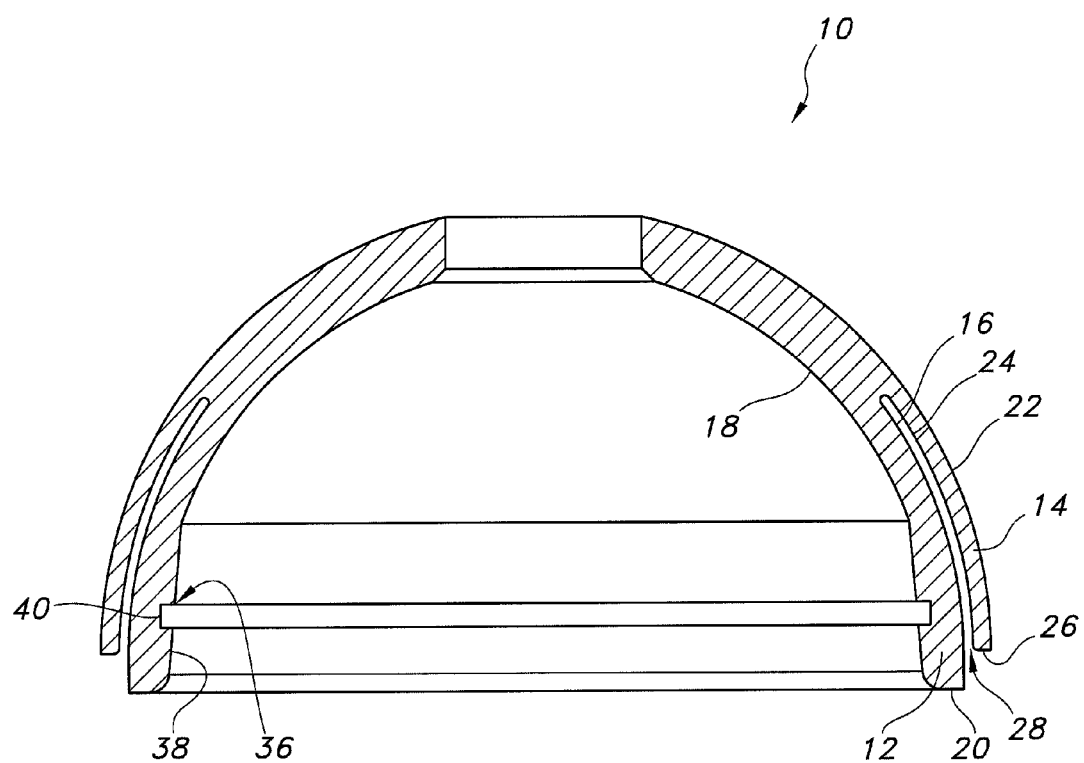
FIG. 2 is a cut-away view of the acetabular shell of FIG. 1.

Turning now to FIG. 2, a sectioned view of the acetabular shell 10 is shown. As shown, the second wall 14 extends outwardly from the inner wall 12, creating the recess 28. Also, as shown in this embodiment, the rim 20 of the first wall 12 extends lower than the rim 26 of the second wall 14.

Figure 4:
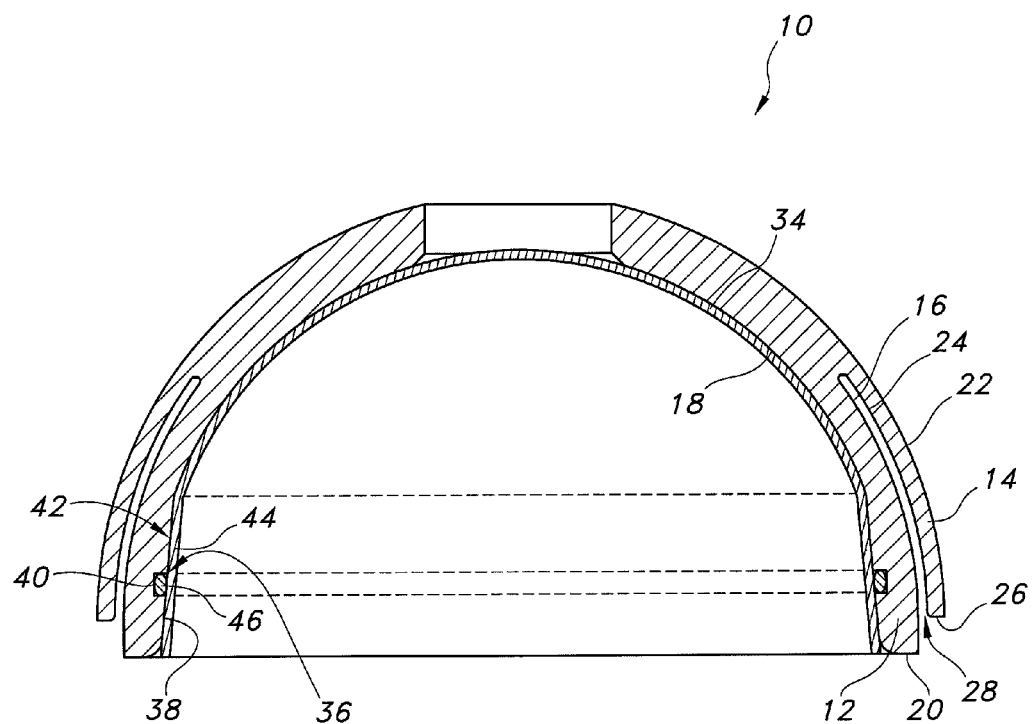
FIG. 4 is a cut-away view of an assembly of the acetabular shell of FIG. 1 and an associated liner.

In some acetabular shell designs, it is desired to have the first wall 12 extend further than the second wall 14 for increased taper engagement of a liner 34 (FIG. 4). In other embodiments, the rims 20, 26 may be in the same plane. In other embodiments, the rim 26 of the second wall 14 may extend lower than the rim 20 of the first wall 12.

The inner surface 18 of the first wall 12 is concave and designed to mate with a liner 34 (FIG. 4). The inner surface 18 includes a locking mechanism 36, which in this embodiment includes a taper 38 and a locking recess 40. The locking mechanism 36 interacts with corresponding features on the liner 34 to lock the liner 34 into the shell 10. In other embodiments, different types of locking mechanisms may be used, for example, only a taper may be used or only a locking ring may be used. In other embodiments, other known locking mechanisms may be used, such as threaded locks, screws, pins, etc. . . .

Figure 3:
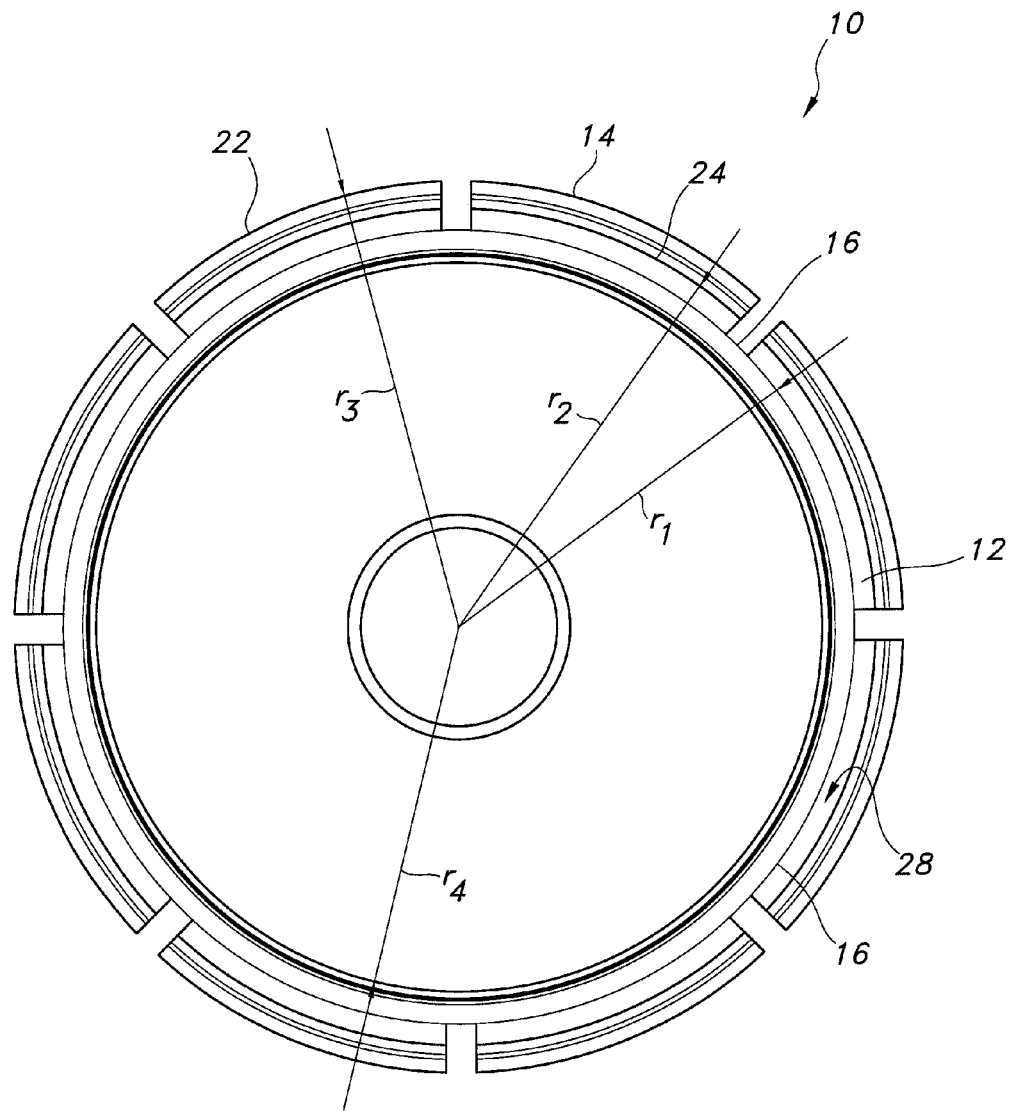
FIG. 3 is a top view of the acetabular shell of FIG. 1.

The outer surface 16 of the first wall 12 is illustrated as being spherical. In certain other embodiments however, the outer surface 16 may be cylindrical in shape. As shown in FIG. 3, the outer surface 16 (whether cylindrical or spherical) has a radius r1. The radius r1 is less than a radius r2 of the inner surface 24 of the second wall 14. The difference between r1 and r2 is the amount that the second wall 14 can be compressed before the first wall 12 is affected. The outer surface 22 of the second wall 14 has a radius r3 that is sized to fit into a prepared acetabulum. As the inner surface 18 of the first wall 12 is designed to mate with a liner 34 as described above, it will have a radius r4 that corresponds to a radius of the liner 34. In some embodiments, a plurality of shells 10 will be provided, having a variety of radiuses r3 to fit into a wide variety of acetabulums. Also, the radius r4 of the inner surface 18 of the first wall 12 may also vary within a set of shells 10 so as to accommodate different liners 34.

FIG. 4 illustrates a shell 10 with a liner 34 assembled into it. As shown, the liner 34 includes a locking mechanism 42 that corresponds with the locking mechanism 36 of the shell 10. In this embodiment, the locking mechanism 42 includes a taper 44 corresponding to the taper 38 of the shell and a locking ring 46 that locks into the locking recess 40 of the shell 10. In some embodiments, the locking mechanism 42 may only include a taper 44 or a locking ring 46, but not both. In yet other embodiments, the taper 44 may not lock into the taper 38 of the shell. The tapers 38, 44 may only be matching tapers so as to allow ease of insertion. In other embodiments, other types of locking mechanisms may be used.

Figure 5:
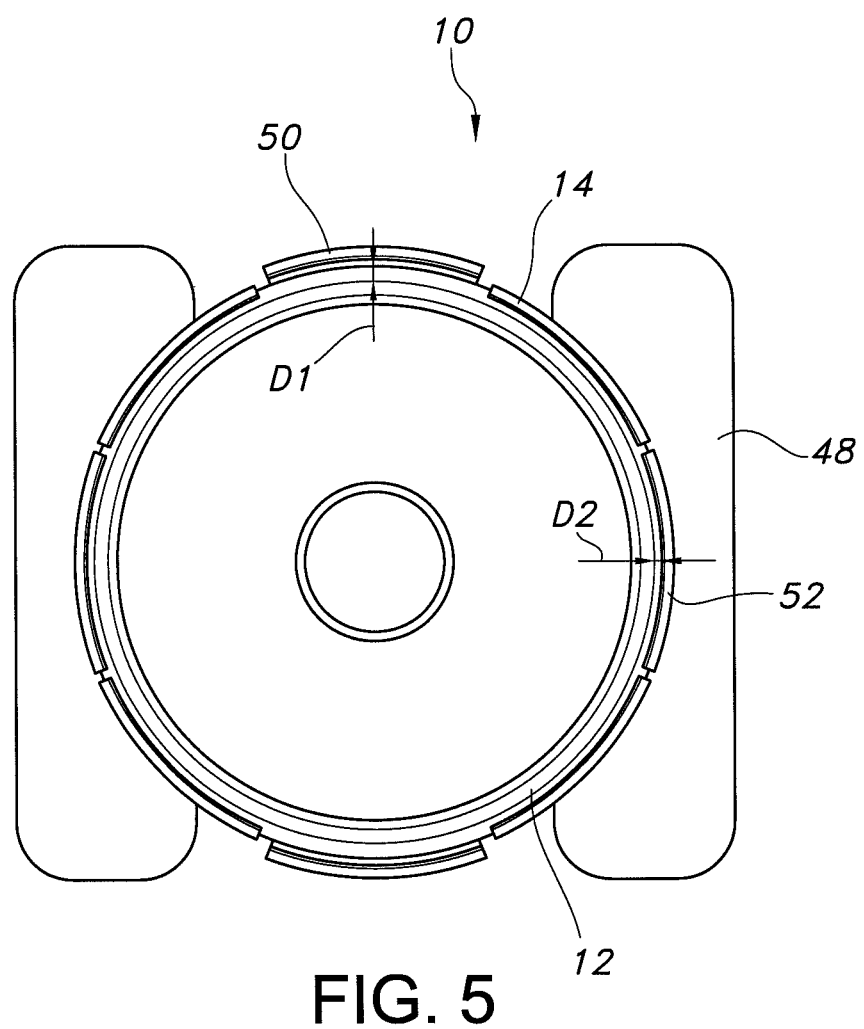
FIG. 5 is a perspective view of the acetabular shell of FIG. 1 inserted into a simulated press-fit acetabulum.

Turning now to FIG. 5, the shell 10 is shown inserted into a simulated press-fit acetabulum 48. As shown, the simulated acetabulum 48 compresses the second wall 14 of the shell 10. As shown in FIG. 5, flange 50 of the second wall 14 is a distance D1 from the inner wall 18. Flange 52 of the second wall 14 is a distance D2 from the inner wall 18. In an uncompressed state, D1 is approximately the same as D2. However, as the second wall 14 is compressed, by the acetabulum 48, D2 becomes less than D1. Even during compression, the inner (or first) wall 12 remains unchanged. Thus, when a liner 34 is inserted, which may be before the insertion of the shell 10 into the acetabulum 48 or after, the locking taper 38 and locking recess 40 are not affected.

Figure 6:
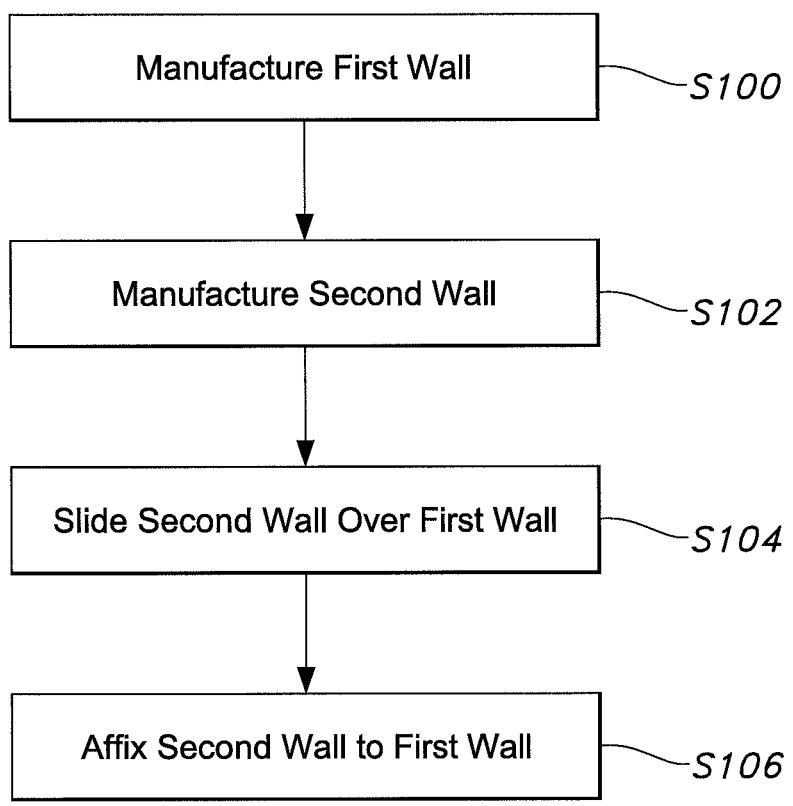
FIG. 6 is a flow chart illustrating a method of manufacturing an acetabular shell according to one embodiment of the present invention.

Turning now to FIG. 6, a method of manufacturing a shell according to one embodiment of the invention will be described. The first wall 12 is manufactured using known methods at step s100. In one embodiment, the first wall 12 is machined. However, other known methods may also be used. At step s102, the second wall 14 is manufactured and then slid onto the first wall 12 (step s104). The second wall 14 is affixed to the first wall 12 via a sintering process or through the addition of an outer porous coating to the shell (step s106). In other embodiments, the first and second walls may be welded together or attached via fasteners.

In other embodiments, the shell 10 may be manufactured as a single piece. The recess 28 may then be cut into the shell 10, creating the first and second walls 12, 14.

In the present embodiment, the shell 10 is made of biocompatible metal, such as titanium, cobalt chrome, stainless steel. The shell 10 may also be made with porous metal, such as GRIPTION®, manufactured by DePuy, Inc. of Warsaw, Ind. As discussed above, the shell 10 may have a sintered coating, such as POROCOAT®, manufactured by DePuy Orthopaedics, Inc. of Warsaw, Ind. Other known porous coatings and materials may also be used. In yet other embodiments, the shell may be made of biocompatible ceramic or plastics, such as ultrahigh molecular weight polyethylene (UHMWPE) or polyether ether ketone (PEEK). In some embodiments the first and second walls 12, 14 are made of the same materials. In other embodiments, the first and second walls 12, 14 may be made of different materials. In those embodiments, the first wall 12 may be made of a stiffer material and the second wall 14 may be made of a more flexible material.

In some embodiments, the liner 34 may be made of biocompatible metals, such as titanium, cobalt chrome, and stainless steel. In other embodiments, the liners 34 may be made of biocompatible polyethylene such as UHMWPE, polyethylene with antioxidants (including UHMWPE with antioxidants), and PEEK. The liners 34 may also be made of biocompatible ceramics, as are known in the art.

While the invention is susceptible to various modifications and alternative forms, a specific embodiment thereof has been shown by way of example in the drawings. It should be understood, however, that there is no intent to limit the invention to the particular form disclosed, but on the contrary, the intention is to cover all modifications, equivalents, and alternatives falling within the spirit and scope of the invention as defined by the appended claims.

The invention claimed is:

1. A method of manufacturing an acetabular shell comprising:

manufacture a first wall of the acetabular shell, the first wall having an outer surface, an inner surface, and a rim, wherein the rim of the first wall extends continuously around an entire circumference of the outer and inner surfaces;

manufacture a flexible second wall of the acetabular shell, the second wall having an outer surface, an inner surface, and a rim;

cutting longitudinal recesses into the flexible second wall creating flanges, wherein the flanges of the flexible second wall are spaced around the circumference, wherein the longitudinal recesses extend to the rim of the second wall of the outer and inner surfaces of the second wall;

slide the second wall of the acetabular shell over the first wall; and affix the second wall to the first wall such that the rim of the first wall is spaced apart from the rim of the flexible second wall.

2. The method of claim 1, wherein affixing the second wall to the first wall comprises affixing the second wall to the first wall via sintering.

3. The method of claim 1, wherein the manufacturing the first wall includes manufacturing an outer wall having a first radius and manufacturing the second wall comprises manufacturing an inner wall having a second radius, the second radius being larger than the first radius.

4. The method of claim 1, wherein the inner surface of the first wall includes a locking mechanism for locking a liner to the shell.

5. The acetabular shell of claim 4, wherein the locking mechanism includes a taper.

6. The acetabular shell of claim 4, wherein the locking mechanism includes a locking recess.

7. The acetabular shell of claim 1, wherein the outer surface of the first wall is convex.

8. The acetabular shell of claim 7, wherein the outer surface of the first wall has a first radius and the inner surface of the second wall has a second radius that is greater than the first radius.

9. The acetabular shell of claim 1, wherein the inner surface of the first wall is concave.

* * * * *